(12) United States Patent
Gambale et al.

(10) Patent No.: US 6,855,160 B1
(45) Date of Patent: Feb. 15, 2005

(54) IMPLANT AND AGENT DELIVERY DEVICE

(75) Inventors: Richard A. Gambale, Tyngsboro, MA (US); Stephen J. Forcucci, Medford, MA (US); Michael F. Weiser, Groton, MA (US); Sean Forde, Watertown, MA (US)

(73) Assignee: C. R. Bard, Inc., Murray Hill, NJ (US)

( * ) Notice: Subject to any disclaimer, the term of this patent is extended or adjusted under 35 U.S.C. 154(b) by 223 days.

(21) Appl. No.: 10/048,694

(22) PCT Filed: Aug. 3, 2000

(86) PCT No.: PCT/US00/21215

§ 371 (c)(1),
(2), (4) Date: Jun. 10, 2002

(87) PCT Pub. No.: WO01/10350

PCT Pub. Date: Feb. 15, 2001

Related U.S. Application Data

(60) Provisional application No. 60/147,094, filed on Aug. 4, 1999, and provisional application No. 60/148,475, filed on Aug. 12, 1999.

(51) Int. Cl.[7] .............................. A61F 11/00; A61F 2/06

(52) U.S. Cl. ....................................... 623/1.11; 606/108

(58) Field of Search ...................... 623/1.11, 1.22–1.23, 623/1.36; 606/107, 108, 191–196, 220

(56) References Cited

U.S. PATENT DOCUMENTS

| | | |
|---|---|---|
| 2,969,963 A | 1/1961 | Brown |
| 3,680,544 A | 8/1972 | Shinnick et al. |
| 3,991,750 A | 11/1976 | Vickery |
| 3,995,617 A | 12/1976 | Watkins et al. |
| 4,307,722 A | 12/1981 | Evans |

(List continued on next page.)

FOREIGN PATENT DOCUMENTS

| | | |
|---|---|---|
| DE | 19703482 | 1/1997 |
| DE | 29619029 | 4/1997 |
| EP | 0 132 387 | 1/1985 |

(List continued on next page.)

OTHER PUBLICATIONS

A. Hassan Khazei et al., "Myocardial Canalization, A new Method of Myocardial Revascularization", *The Annals of Thoracic Surgery*, vol. 6, No. 2, pp. 163–171, Aug. 1968.

(List continued on next page.)

*Primary Examiner*—David J. Isabella
(74) *Attorney, Agent, or Firm*—Kirkpatrick & Lockhart LLP

(57) ABSTRACT

The present invention provides a system for delivering a therapeutic agent in combination with an implanted device to maximize a therapeutic benefit offered by each. Preferably, the therapeutic agent is contained within a solid matrix form such as a pellet or gel to facilitate its handling, and to regulate its rate of dissipation into the tissue after delivery. The implant device is specially configured to receive retain the matrix but permit blood to interact with the matrix so that the agent can be released to the blood in, around the device, and the surrounding tissue. A delivery system comprises an implant delivery device having an obturator capable of piercing the tissue and an agent matrix delivery device to place a matrix form, such as a pellet, into the interior of the implant after it has been implanted. Preferably, the implant delivery device and the matrix delivery device are contained in one apparatus to facilitate delivery of the pellet into the embedded implant. The present invention is useful for treating tissue in any area of the body, especially ischemic tissue experiencing reduced blood flow. The present devices and methods are especially useful for treatment of ischemia of the myocardium. In treatment of the myocardium, the present implant device and matrix combination may be delivered surgically through the epicardium of the heart.

5 Claims, 4 Drawing Sheets

U.S. PATENT DOCUMENTS

| | | |
|---|---|---|
| 4,326,522 A | 4/1982 | Guerrero et al. |
| 4,451,253 A | 5/1984 | Harman |
| 4,461,280 A | 7/1984 | Baumgartner |
| 4,503,569 A | 3/1985 | Dotter |
| 4,546,499 A | 10/1985 | Possis |
| 4,562,597 A | 1/1986 | Possis et al. |
| 4,580,568 A | 4/1986 | Gianturco |
| 4,582,181 A | 4/1986 | Samson |
| 4,641,653 A | 2/1987 | Rockey |
| 4,649,922 A | 3/1987 | Wiktor |
| 4,655,771 A | 4/1987 | Wallsten |
| 4,658,817 A | 4/1987 | Hardy et al. |
| 4,665,918 A | 5/1987 | Garza et al. |
| 4,681,110 A | 7/1987 | Wiktor |
| 4,700,692 A | 10/1987 | Baumgartner |
| 4,718,425 A | 1/1988 | Tanaka et al. |
| 4,733,665 A | 3/1988 | Palmaz |
| 4,768,507 A | 9/1988 | Fischell et al. |
| 4,774,949 A | 10/1988 | Fogarty |
| 4,785,815 A | 11/1988 | Cohen |
| 4,791,939 A | 12/1988 | Maillard |
| 4,813,925 A | 3/1989 | Anderson, Jr. et al. |
| 4,852,580 A | 8/1989 | Wood |
| 4,861,330 A | 8/1989 | Voss |
| 4,889,137 A | 12/1989 | Kolobow |
| 4,904,264 A | 2/1990 | Scheunemann |
| 4,909,250 A | 3/1990 | Smith |
| 4,917,666 A | 4/1990 | Solar et al. |
| 4,920,980 A | 5/1990 | Jackowski |
| 4,950,227 A | 8/1990 | Savin et al. |
| 4,995,857 A | 2/1991 | Arnold |
| 4,997,431 A | 3/1991 | Isner et al. |
| 5,040,543 A | 8/1991 | Badera et al. |
| 5,042,486 A | 8/1991 | Pfeiler et al. |
| 5,047,028 A | 9/1991 | Qian |
| 5,049,138 A | 9/1991 | Chevalier et al. |
| 5,056,517 A | 10/1991 | Fenici |
| 5,087,243 A | 2/1992 | Avitall |
| 5,098,374 A | 3/1992 | Othel-Jacobsen et al. |
| 5,114,414 A | 5/1992 | Buchbinder |
| 5,158,548 A | 10/1992 | Lau et al. |
| 5,167,614 A | 12/1992 | Tessmann et al. |
| 5,172,699 A | 12/1992 | Svenson |
| 5,176,626 A | 1/1993 | Soehendra |
| 5,180,366 A | 1/1993 | Woods |
| 5,190,058 A | 3/1993 | Jones et al. |
| 5,256,146 A | 10/1993 | Ensminger et al. |
| 5,266,073 A | 11/1993 | Wall |
| 5,269,326 A | 12/1993 | Verrier |
| 5,287,861 A | 2/1994 | Wilk |
| 5,290,295 A | 3/1994 | Querals et al. |
| 5,312,456 A | 5/1994 | Reed et al. |
| 5,324,325 A | 6/1994 | Moaddeb |
| 5,328,470 A | 7/1994 | Nabel et al. |
| 5,366,493 A | 11/1994 | Scheiner et al. |
| 5,372,600 A | 12/1994 | Beyar et al. |
| 5,376,071 A | 12/1994 | Henderson |
| 5,380,316 A | 1/1995 | Aita et al. |
| 5,386,828 A | 2/1995 | Owens et al. |
| 5,389,096 A | 2/1995 | Alta et al. |
| 5,391,199 A | 2/1995 | Ben-Haim |
| 5,405,376 A | 4/1995 | Mulier et al. |
| 5,409,004 A | 4/1995 | Sloan |
| 5,409,019 A | 4/1995 | Wilk |
| 5,423,885 A | 6/1995 | Williams |
| 5,425,757 A | 6/1995 | Tiefenbrun et al. |
| 5,429,144 A | 7/1995 | Wilk |
| 5,441,516 A | 8/1995 | Wang et al. |
| 5,452,733 A | 9/1995 | Sterman |
| 5,453,090 A | 9/1995 | Martinez et al. |
| 5,458,615 A | 10/1995 | Klemm |
| 5,464,404 A | 11/1995 | Abela et al. |
| 5,464,650 A | 11/1995 | Berg et al. |
| 5,466,242 A | 11/1995 | Mori |
| 5,476,505 A | 12/1995 | Limon |
| 5,480,422 A | 1/1996 | Ben-Halm |
| 5,487,739 A | 1/1996 | Aebischer et al. |
| 5,501,664 A | 3/1996 | Kaldany |
| 5,514,176 A | 5/1996 | Bosley, Jr. et al. |
| 5,551,427 A | 9/1996 | Altman |
| 5,551,954 A | 9/1996 | Buscemi et al. |
| 5,558,091 A | 9/1996 | Acker et al. |
| 5,562,613 A | 10/1996 | Kaldany |
| 5,562,619 A | 10/1996 | Mirarchi et al. |
| 5,562,922 A | 10/1996 | Lambert |
| 5,569,272 A | 10/1996 | Reed et al. |
| 5,571,168 A | 11/1996 | Toro |
| 5,593,412 A | 1/1997 | Martinez et al. |
| 5,593,434 A | 1/1997 | Williams |
| 5,602,301 A | 2/1997 | Field |
| 5,614,206 A | 3/1997 | Randolph et al. |
| 5,618,563 A | 4/1997 | Berde et al. |
| 5,629,008 A | 5/1997 | Lee |
| 5,635,215 A | 6/1997 | Boschetti et al. |
| 5,643,308 A | 7/1997 | Markman |
| 5,653,756 A | 8/1997 | Clarke |
| 5,655,548 A | 8/1997 | Nelson |
| 5,656,029 A | 8/1997 | Imran et al. |
| 5,662,124 A | 9/1997 | Wilk |
| 5,676,850 A | 10/1997 | Reed et al. |
| 5,682,906 A | 11/1997 | Sterman et al. |
| 5,690,643 A | 11/1997 | Wijay |
| 5,735,897 A | 4/1998 | Buirge |
| 5,741,330 A | 4/1998 | Brauker et al. |
| 5,744,515 A | 4/1998 | Clapper |
| 5,755,682 A | 5/1998 | Knudson et al. |
| 5,756,127 A | 5/1998 | Grisoni et al. |
| 5,762,600 A | 6/1998 | Bruchman et al. |
| 5,769,843 A | 6/1998 | Abela et al. |
| 5,782,823 A | 7/1998 | Mueller |
| 5,785,702 A | 7/1998 | Murphy et al. |
| 5,792,453 A | 8/1998 | Hammond et al. |
| 5,797,870 A | 8/1998 | March et al. |
| 5,807,384 A | 9/1998 | Mueller |
| 5,810,836 A | 9/1998 | Hussein |
| 5,817,101 A | 10/1998 | Fiedler |
| 5,824,049 A | 10/1998 | Ragheb et al. |
| 5,824,071 A | 10/1998 | Nelson et al. |
| 5,827,304 A | 10/1998 | Hart |
| 5,830,502 A | 11/1998 | Dong et al. |
| 5,833,608 A | 11/1998 | Acker |
| 5,840,059 A | 11/1998 | March et al. |
| 5,851,217 A | 12/1998 | Wolff et al. |
| 5,861,032 A | 1/1999 | Subramaniam |
| 5,879,383 A | 3/1999 | Bruchman et al. |
| 5,891,108 A | 4/1999 | Leone et al. |
| 5,893,869 A | 4/1999 | Barnhart et al. |
| 5,899,915 A | 5/1999 | Saadat |
| 5,968,052 A | 10/1999 | Sullivan, III et al. |
| 5,971,993 A | 10/1999 | Hussein |
| 5,980,514 A | 11/1999 | Kupiecki et al. |
| 5,980,548 A | 11/1999 | Evans et al. |
| 6,045,565 A | 4/2000 | Ellis et al. |
| 6,051,001 A | 4/2000 | Borghi |
| 6,053,924 A | 4/2000 | Hussein |
| 6,086,582 A | 7/2000 | Altman et al. |
| 6,197,324 B1 | 3/2001 | Crittenden |
| 6,248,112 B1 | 6/2001 | Gambale et al. |
| 6,251,079 B1 | 6/2001 | Gambale et al. |
| 6,251,418 B1 | 6/2001 | Ahern et al. |
| 6,263,880 B1 | 7/2001 | Parker et al. |

| | | | |
|---|---|---|---|
| 6,277,082 B1 | 8/2001 | Gambale | |
| 6,432,126 B1 | 8/2002 | Gambale et al. | |
| 6,447,522 B2 | 9/2002 | Gambale et al. | |
| 6,458,092 B1 | 10/2002 | Gambale et al. | |

FOREIGN PATENT DOCUMENTS

| | | |
|---|---|---|
| EP | 0 363 661 | 4/1990 |
| EP | 0 515 867 A2 | 12/1992 |
| EP | 0 584 959 A2 | 7/1993 |
| EP | 0 490 459 A1 | 10/1994 |
| EP | 0 714 640 A1 | 6/1996 |
| EP | 0 717 969 A2 | 6/1996 |
| EP | 0 732 089 A2 | 9/1996 |
| EP | 0 812 574 A2 | 12/1997 |
| EP | 0 830 873 A2 | 3/1998 |
| EP | 0 853 921 A2 | 7/1998 |
| EP | 0 953 320 A2 | 11/1999 |
| EP | 1 078 610 | 2/2001 |
| FR | 1514319 | 1/1967 |
| FR | 2725615 | 10/1994 |
| FR | 1278965 | 1/1996 |
| RU | 2026640 C1 | 1/1995 |
| RU | 2063179 C1 | 7/1996 |
| WO | WO 89/01798 | 3/1989 |
| WO | WO 90/06723 | 6/1990 |
| WO | WO 91/15254 | 10/1991 |
| WO | WO 94/05265 | 3/1994 |
| WO | WO 94/27612 | 12/1994 |
| WO | WO 96/13303 | 10/1995 |
| WO | WO 95/33511 | 12/1995 |
| WO | WO 96/39830 | 5/1996 |
| WO | WO 96/40368 | 6/1996 |
| WO | WO 96/20698 | 7/1996 |
| WO | WO 97/16169 | 10/1996 |
| WO | WO 97/42910 | 7/1997 |
| WO | WO 97/32551 | 9/1997 |
| WO | WO 97/38730 | 10/1997 |
| WO | WO 97/44071 | 11/1997 |
| WO | WO 97/45105 | 12/1997 |
| WO | WO 97/47253 | 12/1997 |
| WO | WO 98/05307 | 2/1998 |
| WO | WO 98/08456 | 3/1998 |
| WO | WO 98/16644 | 4/1998 |
| WO | WO 98/23228 | 6/1998 |
| WO | WO 98/25533 | 6/1998 |
| WO | WO 98/29148 | 7/1998 |
| WO | WO 98/32859 | 7/1998 |
| WO | WO 98/46115 | 10/1998 |
| WO | WO 99/21510 | 5/1999 |
| WO | WO 99/38459 | 8/1999 |
| WO | WO 99/53863 | 10/1999 |

OTHER PUBLICATIONS

Alfred Goldman et al., "Experimental Methods for Producing a Collateral Circulation to the Heart Directly from the Left Ventricle", Journals of Thoracic Surgery, vol. 31, No. 3, pp. 364–374, Mar. 1956.

A. Sachinopoulou et al., "Invited Review Transmyocardial Revascularization", Lasers in Medical Science, 1995, vol. 10, pp. 83–91, Sep. 1995.

B. Schumacher et al., Induction of Neoangiogenesis in Ischemic Myocardium by Human Growth Factors, First Clinical Results of a New Treatment of Coronary Heart Disease, Clinical Investigation and Reports, pp. 645–650, Dec. 1997.

Charles T. Dotter, Transluminally–placed Coilspring Endarterial Tube Grafts: Long–term Patency in Canine Popliteal Artery, Investigative Radiology, pp. 329–332, Sep.–Oct. 1969.

C. Massimo et al., Myocardial Revascularization By a New Method of Carrying Blood Directly from the Left Ventricular Cavity into the Coronary Circulation, Journals of Thoracic Surgery, vol. 34, No. 2, pp. 257–264, Aug. 1957.

Garrett Lee et al., Feasibility of Intravascular Laser Irradiation for In vivo Visualization and therapy of Cardiocirculatory Diseases, American Heart Journal., vol. 103 No. 6, pp. 1076–1077.

Garrett Lee et al., Laser–Dissolution of Coronary Atherosclerotic Obstruction, American Heart Journal, vol. 102, No. 6, part 1, pp. 1074–1075, Dec. 1981.

George S. Abela et al., Use of Laser Radiation to Recanalize Totally Obstructed Coronary Arteries (Abstract), Journal American College Cardiology 1983:1(2):691.

George S. Abela et al., Laser Revascularization: What Are Its Prospects?, Journal of Cardiovascular Medicine, pp. 977–984, Sep. 1983.

Isam N. Anabtawi et al., Experimental Evaluation of Myocardial Tunnelization as a Method of Myocardial Revascularization, Journal of Thoracic and Cardiovascular Surgery, vol. 58, No. 5, pp. 638–646, Nov. 1969.

John E. Hershey et al., Transmyocardial Puncture Revascularization, Geriatrics, pp. 101–108, Mar. 1969.

Ladislav Kuzela et al. Experimental Evaluation of Direct Transventricular Revascularization, Journal of Thoracic Cardiovascular Surgery, vol. 57, No. 6, pp. 770–773, Jun. 1969.

Mahmood Mirhoseini et al., Myocardial Revascularization by Laser: A Clinical Report; Lasers in Surgery and Medicine 3:241–245 (1983).

Mahmood Mirhoseini et al. Revascularization of the Heart by Laser; Journal of Microsurgery, pp. 253–260, Jun. 1981.

Mahmood Mirhoseini et al., Transventricular Revascularization by Lasers in Surgery and Medicine, vol. 2, pp. 1987–198, 1982.

Mahmood Mirhoseini et al., Clinical Report: Laser Myocardial Revascularization, Lasers in Surgery and Medicine vol., 6, pp. 459–461, 1986.

Mahmood Mirhoseini et al., New Concepts in Revascularization of the Myocardium, The Annals of Thoracic Surgery, vol. 45, No. 4, pp. 415–420, Apr. 1988.

P. Walter et al., Treatment of Acute Myocardial Infarction by Transmural Blood Supply from the Ventricular Cavity, Department of Surgery and Department of Radiology of the Hanover Medical School, Hanover, pp. 130–138, (1971).

Peter Whittaker, et al., Transmural Channels Can Protect Ischemic Tissue, Assessment of Long–term Myocardial Response to Laser and Needle–Made Channels, Circulation, vol. 93, No. 1, pp. 143–152, Jan.1996.

P.K. Sen. et al., Further Studies in Multiple Transmyocardial Acupuncture as a Method of Myocardial Revascularization, Surgery, vol., 64, No. 5, pp. 861–870, No. 1968.

P.K. Sen, et al, Transmyocardial Acupuncture, A New Approach to Myocardial Revascularization; Journal of Thoracic and Cardiovascular Surgery, vol. 50, No. 2, pp. 181–189, Aug. 1965.

R.I. Hardy et al., Regional Myocardial Blood Flow and Cardiac Mechanics in Dog Hearts with $CO_2$ Laser–Induced Intramyocardial Revascularization, Basic Research Cardiology, 85:179–197 (1990).

Roque Pifarre et al., Myocardial Revascularization by Transmyocardial Acupuncture: A Physiologic Impossibility; Journal of Thoracic and Cardiovascular Surgery; vol. 58, No. 3, pp. 424–429, Sep. 1969.

Valluvan Jevanandam et al., Myocardial Revascularization by Laser–Induced Channels, Surgical Forum vol. VL, American College of Surgeons 76th Clinical Congress, vol. 4, pp. 225–227, Oct. 1990.

Neil B. Ingels, et al., Measurement of Midwall Myocardial Dynamics in Intact Man by Radiography of Surgically Implanted Markers, Circulation, vol. 52, pp. 859–867 (Nov. 1975).

Dr. Joachim Burhenne, "Less Invasive Medicine: Historical Perspectives", *Boston Scientific Home Page, Corporate Information/Special Report*, pp. 1–11.

Mark Freed, M.D. et al., "The New Manuel of Interventional Cardiology", *Physicians' Press, Division of Cardiologym, William Beaumont Hospital, Royal Oak, Michigan*, pp. 645–660 (1996).

A. Michael Lincoff, M.D. et al. "Local Drug Delivery for the Prevention of Restenosis Fact, Fancy and Future", *Cleveland Clinic Foundation, The Department of Cardiology, Cleveland, Ohio*, vol. 90, No. 4, pp. 2070–2084 (1994).

Reimer Reissen, M.D. et al., "Prospects for Site–Specific Delivery of Pharmacologic and Molecular Therapies", *JAAC*, vol. 23, No. 5.

Bruce F. Waller, M.D., "Anatomy, Histology, and Pathology of the Major Epicardial Coronary Arteries Relevant to Echocardiographic Imaging Techniques", *J. A. Soc. Echo.*, vol. 2, pp. 232–252 (1989).

Robert L. Wilensky et al., "Methods and Devices for Local Drug Delivery in Coronary and Peripheral Arteries", *TCM*, vol. 3, No. 5 (1993).

M. A. Martinelli, et al., "Intraluminal Ultrasound Guidance of Transverse Laser Coronary Arthrectomy", *Optical Fibers in Medicine*, vol. 1201, pp. 68–78, (1990).

U.S. Appl. No. 09/073,118, filed May 5, 1998, Gambale.
U.S. Appl. No. 09/159,834, filed Sep. 24, 1998, Cafferata.
U.S. Appl. No. 09/162,547, filed Sep. 29, 1998, Gambale.
U.S. Appl. No. 09/211,332, filed Dec. 15, 1998, Gambale et al.
U.S. Appl. No. 09/299,795, filed Apr. 26, 1999, Ahern.
U.S. Appl. No. 09/328,808, filed Jun. 9, 1999, Ahern.
U.S. Appl. No. 09/368,119, filed Aug. 4, 1999, Tedeschi et al.
U.S. Appl. No. 09/743,695, filed Apr. 12, 2001, Weiser et al.
U.S. Appl. No. 09/743,726, filed Apr. 12, 2001, Gambale et al.
U.S. Appl. No. 09/774,319, filed Jan. 31, 2001, Gambale et al.
U.S. Appl. No. 09/774,320, filed Jan. 31, 2001, Gambale et al.
U.S. Appl. No. 09/888,757, filed Jun. 25, 2001, Ahern et al.
U.S. Appl. No. 09/990,644, filed Nov. 21, 2001, Gambale et al.
U.S. Appl. No. 10/048,205, filed May 2, 2002, Gambale.

IMPLANT AND AGENT DELIVERY DEVICE

This application claims benefit to U.S. provisional application Ser. No. 60/147,094 filed Aug. 4, 1999 and claims benefit to U.S. provisional application Ser. No. 60/148,475 filed Aug. 12, 1999.

FIELD OF THE INVENTION

The present invention relates to delivery of a therapeutic agent to tissue in combination with an implant device. Specifically, the agent is contained in a matrix form capturable within the implant device to provide the therapeutic advantages provided by both in a single treatment.

BACKGROUND OF THE INVENTION

Tissue becomes is ischemic it is deprived of adequate blood flow. Ischemia causes pain in the area of the affected tissue and, in the case of muscle tissue, can interrupt muscular function. Left untreated, ischemic tissue can become infarcted and permanently non-functioning. Ischemia can be caused by a blockage in the vascular system that prohibits oxygenated blood from reaching the affected tissue area. However, ischemic tissue can be revived to function normally despite the deprivation of oxygenated blood because ischemic tissue can remain in a hibernating state, preserving its viability for some time. Restoring blood flow to the ischemic region serves to revive the ischemic tissue. Although ischemia can occur in various regions of the body, often myocardial tissue of the heart is affected by ischemia. Frequently, the myocardium is deprived of oxygenated blood flow due to coronary artery disease and occlusion of the coronary artery, which normally provides blood to the myocardium. The ischemic tissue causes pain to the individual affected.

Treatment of myocardial ischemia has been addressed by several techniques designed to restore blood supply to the affected region. A conventional approach to treatment of ischemia has been to administer anticoagulant with the objective of increasing blood flow by preventing formation of thrombus in the ischemic region.

Another conventional method of increasing blood flow to ischemic tissue of the myocardium is coronary artery bypass grafting (CABG). One type of CABG involves grafting a venous segment between the aorta and the coronary artery to bypass the occluded portion of the artery. Once blood flow is redirected to the portion of the coronary artery beyond the occlusion, the supply of oxygenated blood is restored to the area of ischemic tissue.

Early researchers, more than thirty years ago, reported promising results for revascularizing the myocardium by piercing the muscle to create multiple channels for blood flow. Sen, P. K. et al., "Transmyocardial Acupuncture—A New Approach to Myocardial Revascularization", *Journal of Thoracic and Cardiovascular Surgery*, Vol. 50, No. 2. August 1965, pp. 181–189. Although researchers have reported varying degrees of success with various methods of piercing the myocardium to restore blood flow to the muscle (which has become known generally as transmyocardial revascularization or TMR), many have faced common problems such as closure of the created channels. Various techniques of perforating the muscle tissue to avoid closure have been reported by researchers. These techniques include piercing with a solid sharp tip wire, or coring with a hypodermic tube. Reportedly, many of these methods produced trauma and tearing of the tissue that ultimately led to closure of the channel.

An alternative method of creating channels that potentially avoids the problem of closure involves the use of laser technology. Researchers have reported success in maintaining patent channels in the myocardium by forming the channels with the heat energy of a laser. Mirhoseini, M. et al., "Revascularizatlon of the Heart by Laser", *Journal of Microsurgery,* Vol. 2, No. 4, June 1981, pp. 253–260. The laser was said to form channels in the tissue that were clean and made without tearing and trauma, suggesting that scarring does not occur and the channels are less likely to experience the closure that results from healing. U.S. Pat. No. 5,769,843 (Abela et al.) discloses creating laser-made TMR channels utilizing a catheter based system. Abela also discloses a magnetic navigation system to guide the catheter to the desired position within the heart. Aita U.S. Pat. Nos. 5,380,316 and 5,389,096 disclose another approach to a catheter based system for TMR.

Although there has been some published recognition of the desirability of performing TMR in a non-laser catheterization procedure, there does not appear to be evidence that such procedures have been put into practice. U.S. Pat. No. 5,429,144 (Wilk) discloses inserting an expandable implant within a preformed channel created within the myocardium for the purposes of creating blood flow into the tissue from the left ventricle.

Performing TMR by placing stents in the myocardium also is disclosed in U.S. Pat. No. 5,810,836 (Hussein et al.). The Hussein patent discloses several stent embodiments that are delivered through the epicardium of the heart, into the myocardium and positioned to be open to the left ventricle. The stents are intended to maintain an open channel in the myocardium through which blood enters from the ventricle and perfuses into the myocardium.

Angiogenesis, the growth of new blood vessels in tissue, has been the subject of increased study in recent years. Such blood vessel growth to provide new supplies of oxygenated blood to a region of tissue has the potential to remedy a variety of tissue and muscular ailments, particularly ischemia. Primarily, study has focused on perfecting angiogenic factors such as human growth factors produced from genetic engineering techniques. It has been reported that injection of such a growth factor into myocardial tissue initiates angiogenesis at that site, which is exhibited by a new dense capillary network within the tissue. Schumacher et al., "Induction of Neo-Angiogenesis in Ischemic Myocardium by Human Growth Factors", *Circulation,* 1998; 97:645–650.

SUMMARY OF THE INVENTION

The present invention provides a system for delivering a therapeutic agent in combination with an implantable device to maximize a therapeutic benefit offered by each. Preferably, the therapeutic agent is contained within a solid matrix form such as a pellet or gel to facilitate its handling and to regulate its rate of dissipation into the tissue after delivery. The implant device is specially configured to receive and retain the pellet but permit blood to interact with the pellet so that the agent can be released to the blood in and around the device and the surrounding tissue. A delivery system comprises an implant delivery device having an obturator capable of piercing the tissue and an agent matrix delivery device to place a matrix form, such as a pellet, into the interior of the implant after it has been implanted. Preferably, the implant delivery device and the pellet delivery device are contained in one apparatus to facilitate delivery of the pellet into the embedded implant.

The present invention is useful for treating tissue in any area of the body, especially ischemic tissue experiencing reduced blood flow. The present devices and methods are especially useful for treatment of ischemia of the myocardium. In treatment of the myocardium, the present implant device and pellet combination may be delivered surgically through the epicardium of the heart.

With specific agents and a particular configuration of the implant device, revascularization by angiogenesis and vessel recruitment can be encouraged in the ischemic tissue by use of the present invention. A wide range of therapeutic agents conducive to revascularization can be introduced via the matrix pellet including: growth factors; gene therapies or other natural or engineered substances that can be formed or added to the pellet. The pellet formation is well known in the medical field and typically comprises an inert powder pressed together to form a tablet or pill-like article.

The implant device also provides therapeutic benefit to the subject tissue in several ways. First the structure of the implant device provides an interior cavity within the tissue which permits blood to pool, mix with the agents of the matrix and coagulate. The coagulation occurs in and around the device as part of the coagulation cascade, that will eventually lead to new vessel formation and recruitment. Furthermore, the presence of a device in the moving tissue of a muscle such as the myocardium, creates an irritation or injury to the surrounding tissue which further promotes an injury response and the coagulation cascade that leads to new vessel growth. Additionally the implant causes a foreign body response, which causes inflammation attracting macrophages, which cause secretion of growth factors. Suitable implant devices should be flexible, define an interior, be anchorable within tissue and permit fluid such as blood to transfer between the surrounding tissue and the interior of the device. Examples of tissue implant devices are disclosed in pending U.S. patent application Ser. Nos. 09/164,163, 09/164,173, 09/211,332 and 09/299,795, all of which are herein incorporated by reference. Delivery of therapeutic agents in a pellet form are discussed in pending U.S. application Ser. Nos. 08/993,586 and 09/116,313 and 09/159,834, all of which are herein incorporated by reference.

It is an object of the present invention to provide an agent delivery system that permits the delivery of an agent in combination with an implant device into tissue.

It is another object of the present invention to provide an implant device configured to retain an agent matrix form, such as a pellet containing a therapeutic substance while it is implanted in tissue.

It is another object of the invention to provide a delivery method for sequentially delivering the implant device and a matrix containing a therapeutic substance that is. relatively simple and effective.

It is another object of the present invention to provide a method for delivering an implant device and matrix containing a therapeutic agent that utilizes a simplified delivery device.

It is yet another object of the present invention to provide a dual step delivery system contained in one apparatus and associated method for sequentially delivering an implant then an agent suspending matrix form into the interior of the implant device placed in the tissue.

BRIEF DESCRIPTION OF THE DRAWINGS

The foregoing and other objects and advantages of the invention will be appreciated more fully from the following further description thereof, with reference to the accompanying diagrammatic drawings wherein.

DESCRIPTION OF THE ILLUSTRATIVE EMBODIMENTS

Figure 1:
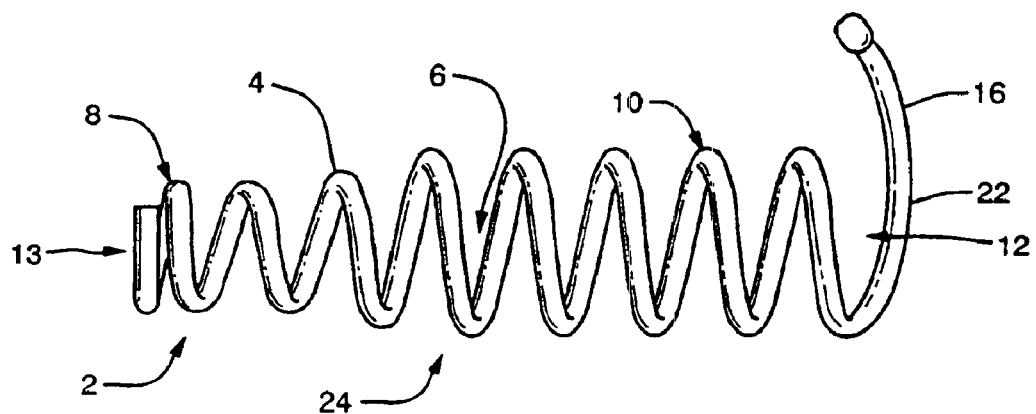
FIG. 1. is a side view of an implant device configured to accept a matrix.

FIG. 1 shows a side view of an implant device 2 of the present invention. In a preferred embodiment the implant device 2 comprises a flexible helical coil having a plurality of individual coils 4 that define an interior 6. The device preferably has a distal region 8 and proximal region 10. The coils at the distal region 8 define a diameter that is smaller than that defined by the coils of proximal region 10. However, an agent carrying matrix, such as a pellet, may be inserted through proximal opening 12 into the proximal region 10 of the implant. The coils 4 of the distal region 8 are sized smaller than the pellet so that the pellet cannot slip out of the implant through the distal region. In the present application, proximal is understood to mean the direction leading external to the patient and distal is understood to mean a direction leading internally to the patient.

It should be noted that the agent carrying matrix may, but need not be a pellet form. A pellet may comprise a pill or tablet like article formed from inert substances. compressed together, the substances are normally absorbable in the body. The pellet may be formed with a radiopaque seed to provide radiographic visibility of the implant location. In a preferred embodiment the pellet may have a generally cylindrical shape having a diameter on the order of 0.060 inch and a thickness of 0.028 inch.

Figure 2:
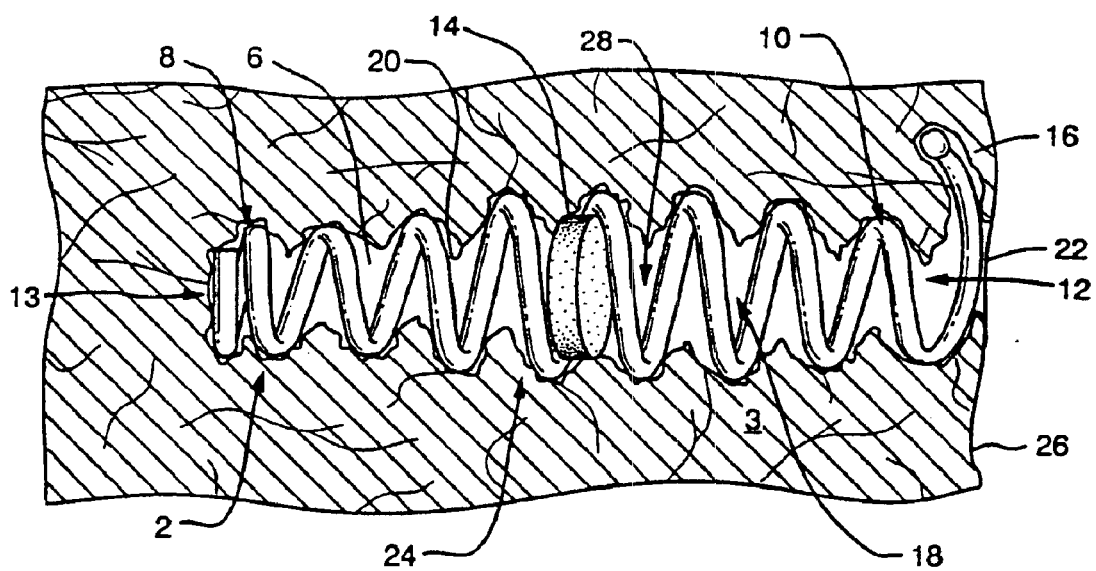
FIG. 2. is a side view of an implant device containing a matrix.

FIG. 2 shows the implant device 2 implanted in tissue 3 and having captured with its interior 6 an agent carrying matrix 14, such as a pellet. The implant device maintains a cavity 18 within the tissue defined by the interior 6 of the device where the matrix may reside and blood may pool and mix with agents contained in the matrix 14. After the device is implanted in tissue, by steps which will be described in detail below, a tail 16 joined to the proximal end 22 of the device 2 serves to prevent the device from migrating out of the tissue. The tail may comprise a variety of configurations but should extend to have a profile that is greater than the diameter of the coils along the body 24 of the device. The tail projects into the tissue and is submerged beneath the surface 26 of the tissue 3 to prevent axial migration as well as rotation of the device, which could permit the device to move from the tissue location.

In one implant embodiment shown in FIG. 2, the pellet may be maintained in position within the interior 6 of the device 2 by reducing the diameter of the coils 4 of the proximal portion 10 of the device after the matrix 14 has been inserted. As mentioned above, the coils of the distal portion 8 are pre-formed to have a diameter that is smaller than the lateral extent of the pellet to prevent distal migration out of the device. The proximal portion coils 10 may be reduced in diameter by crimping by sterilized forceps after the implant device and matrix are delivered to the tissue. The reduced diameter coils of the proximal portion 10 and a distal portion 8 of the device leave a capturing portion 28 at the center of the device where the matrix will reside. The matrix may move slightly within this capturing portion 28 but will not migrate from either the proximal end 12 or distal end 13 of the device.

Preferably, the matrix is restrained in the implant by a close or a friction fit between the pellet and the inside diameter of the coils 4. So configured, there would be no clearance around an installed matrix and the implant device coils. The friction fit permits the matrix to be delivered into the device and retained without crimping the proximal coils behind the matrix to retain it, thereby eliminating an additional step after delivery. In this case, the implant device may be configured to have coils of approximately constant diameter. When a matrix, such as a pellet, is configured to have zero clearance with the inside diameter of the device, the pellet may be shaped to have a smaller profile distal end (leading edge) to be more easily insertable into the narrow opening of the device. An example of such a shape would be a cone shape pellet (not shown).

In treating the myocardium of the heart a preferred device length is on the order of approximately 7 mm–8 mm. The device may be made from any implantable material such as surgical grades of stainless steel or a nickel titanium alloy. The filament of material from which the coils are formed may have any cross-sectional shape. A round filament may have a diameter on the order of 0.006 inch to 0.010 inch.

Figure 3:
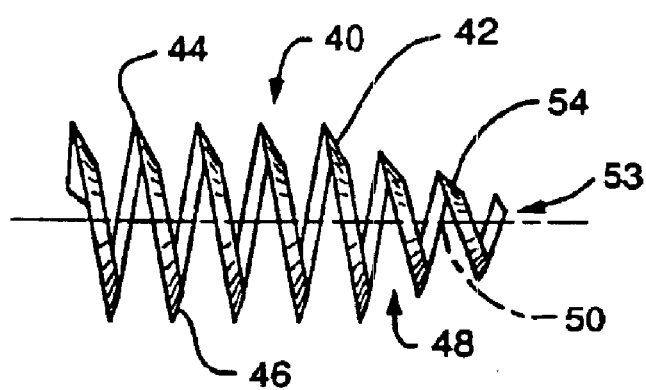
FIG. 3 is a side view of an alternate embodiment of the tissue implant device.
Figure 4:
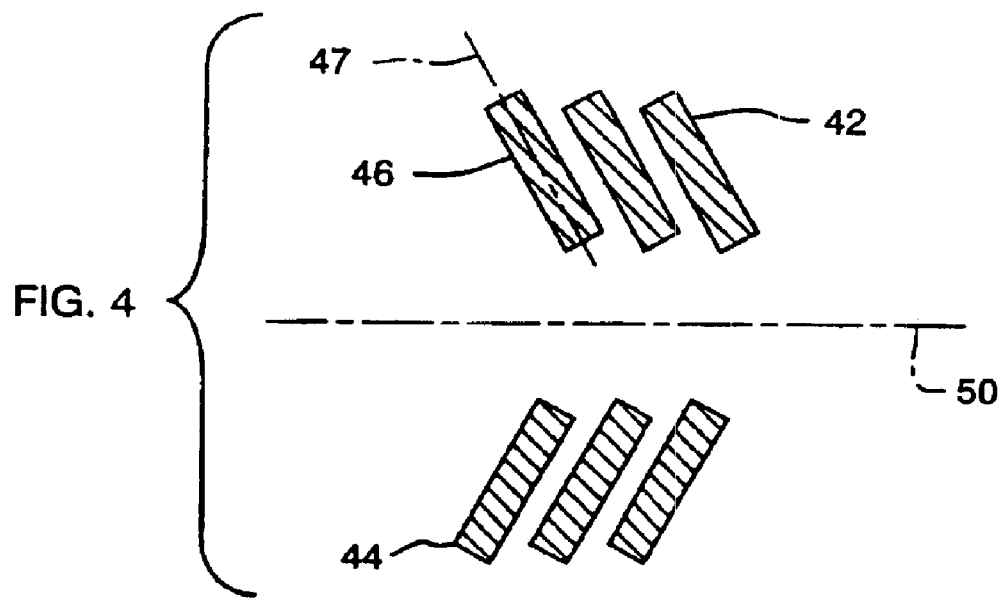
FIG. 4 is a partial sectional view of the tissue implant device shown in FIG. 3.

Alternatively, the implant may be formed from a filament having a rectangular crosssectional shape. FIG. 3 shows an embodiment of a tubular implant device 40 formed from a filament 42 of rectangular cross-section such as a strand of flat wire. As shown in FIG. 4, the coil is formed so that the major cross-sectional axis 47 of the rectangular wire is oriented at an acute angle to the longitudinal axis 50 of the coil 40. The orientation gives each turn 46 of the coil a projecting edge 44, which tends to claw into tissue to serve as an anchoring mechanism for the device. The implant device may have coils of substantially the same diameter sized to closely surround a matrix inserted into the implant interior. At least the most distal coil 54 should be wound to a smaller diameter that will frictionally engage the surface of the obturator delivery device as is discussed in detail below.

In addition to being retained by surrounding coils of the device, the matrix is supported in position within the device and within the capturing portion 28 by herniation points 20 of the surrounding tissue 3, as shown in FIG. 2. After insertion of the device, surrounding tissue attempts to resume its previous position, collapsing around the individual coils 4 of the device and tending to herniate at points 20 through the spaces between the coils 4. The herniation points extending into the interior 6 of the device 2 engage the matrix 14 to help maintain it is position so that it does not migrate through either end or through the spaces between the coils 4.

With implants of the first embodiment in which the proximal coils are crimped after pellet delivery, it has proven desirable to have approximately 0.002 inch of clearance between the matrix and the inside diameter of the coils 4 in the larger coiled proximal region 10 (as well as the captured portion 28—after the proximal coils 10 have been crimped). Therefore, the preferable inside diameter of the coils 4 through a proximal region 10 is on the order of 0.065 inch. It has also been found desirable to have the restraining coils of small diameter, such as those at the distal portion 8, to be approximately 0.002 inch smaller in inside diameter than the diameter of the matrix. Therefore, the preferable inside diameter for distal coils 8 is approximately 0.055 to 0.056 inch. Likewise, it is preferable to have spacing between adjacent coils 4 of the implant device 2 to be no more than approximately 0.026 inch so that the matrix does not migrate through the space between the coils. In preferred implant embodiments having coils of constant diameter, the coils may define an inside diameter of approximately 0.061–0.062 inch to closely surround a pellet of 0.060 inch diameter.

Figure 5A:
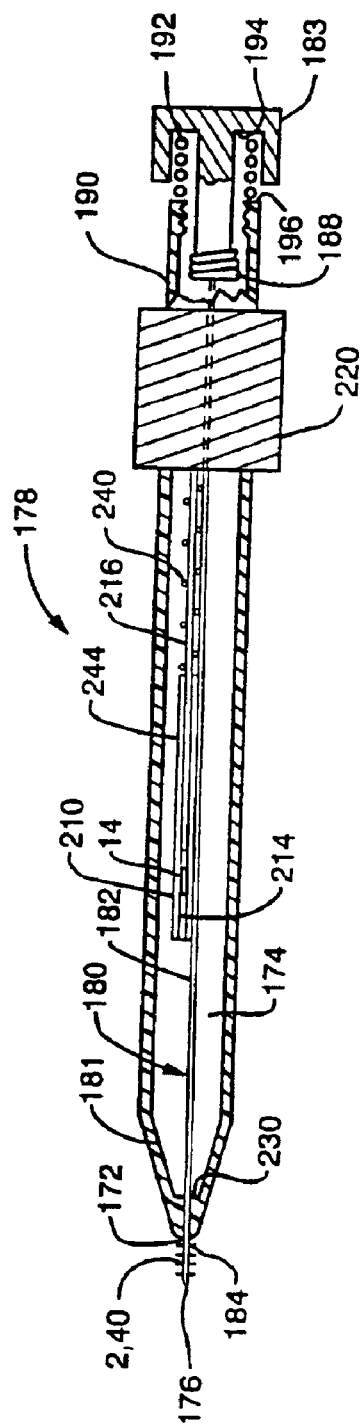
FIG. 5A. is a partial sectional side view of an implant delivery device delivering an implant device.
Figure 5B:
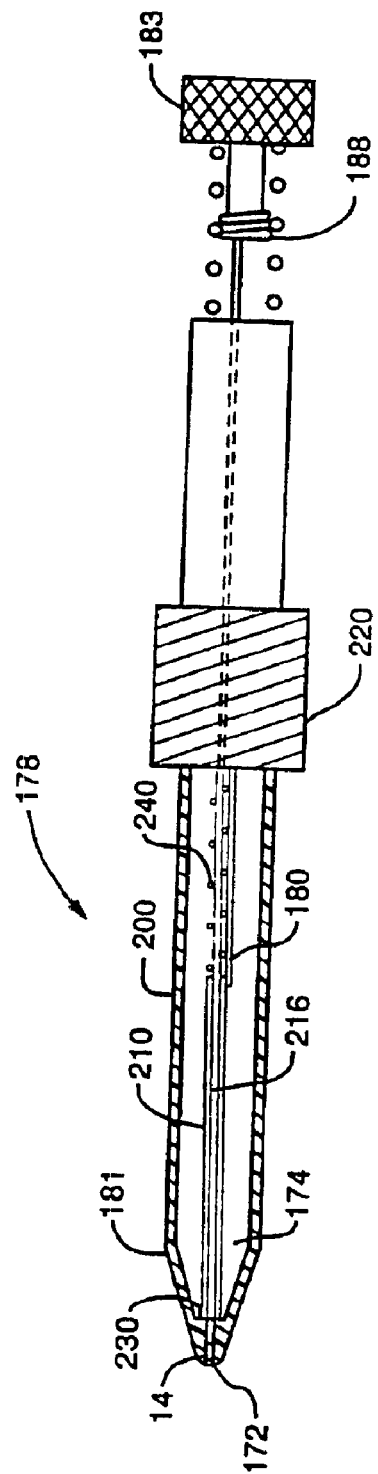
FIG. 5B. is a partial sectional side view of the implant delivery device shown in FIG. 5A, delivering an agent carrying matrix into the implanted device.
Figure 5C:
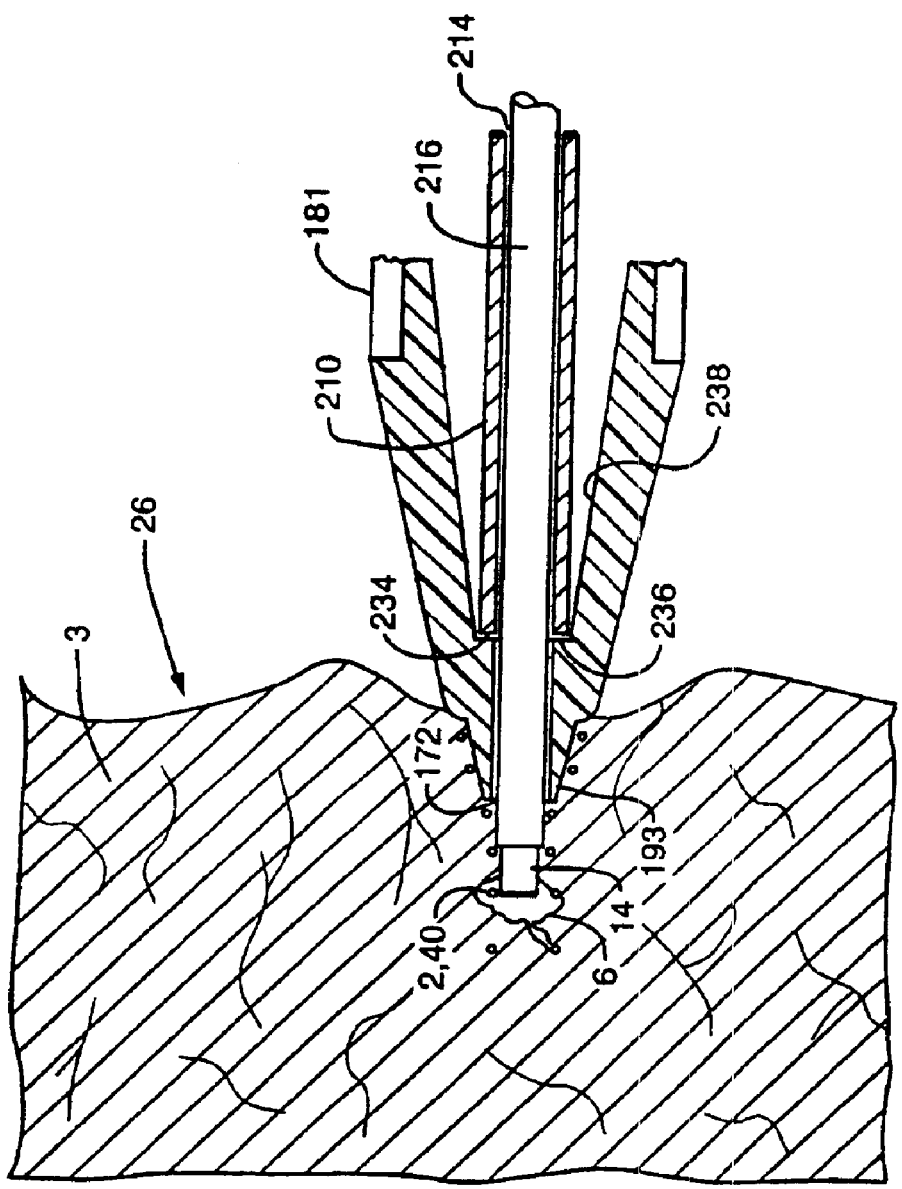
FIG. 5C. is a detail of the distal tip of an implant delivery device shown in FIG. 5B delivering an agent matrix into an implant.

The implant devices 2 and 40 of the present invention are preferably delivered to their intended tissue location surgically. FIGS. 5A–5C show an example of a surgical delivery device 178 that may be used to deliver the implants into tissue such as that of the myocardium of the heart. The delivery device 178, shown in FIG. 5A is, generally, a hollow rigid tubular structure formable or machined from a polymer that comprises an obturator 180 for delivering the implant and a matrix delivery tube 210 for delivering the agent matrix 14. Both are independently advanceable and retractable through the interior 174 of the device 178 to a distal port 172. The distal end 181 of the device 178 is shown in detail in FIG. 5C.

The obturator includes a spring loaded main shaft 182, by which it can be gripped and manipulated by a threaded knob 183. The obturator 180 also includes a reduced diameter device support section 184 having a sharp distal tip 186 adapted to pierce tissue. The diameter of the shaft segment 184 is selected to fit closely within the interior 6 of the devices 2 and 40. Preferably, the obturator is configured so that the device is held onto the obturator only by a close frictional fit. The reduced diameter distal coil of an implant frictionally engages the support section 184. The proximal end of the segment 184 may terminate in a shoulder (not shown) formed at the junction of a proximally adjacent, slightly enlarged diameter portion 190 of the shaft. When the implant device 2 is mounted on the obturator 180, the proximal end of the device may bear against the shoulder. Alternatively, the distal end of the device support segment 184 may include a radially projecting pin (not shown) dimensioned to project and fit between adjacent turns of the coils 4. The pin engages the coils in a thread-like fashion so that after the assembly has been inserted into the tissue, the obturator 180 can be removed simply by unscrewing the obturator to free it from the implanted coil. Alternatively, the tip of the distal most coil of the implant may be deformed to project radially inward so as to catch a small receiving hole formed in the distal end of the support segment 184.

The matrix delivery tube 210 has slidable within its interior lumen 214 a push rod 216. The push rod is slidably controllable by slide 220, slidably mounted to the exterior of the body 200 of the device 178. A matrix pellet is sized to be retained in the lumen 214 of the delivery tube by the resilient force of the radially flexible tube against the matrix. The restraining force of the tube on the pellet can be easily over come by advancement of the pushrod through the delivery tube 210. Advancement of slide 220 serves to move both the delivery tube 210 and pushrod 216 together in unison in the distal direction through the interior 174 until distal end 234 bottoms out against distal stop 236, an annular ridge encircling the exit port 172 of the device. After the distal end bottoms against the stop, distal movement of the delivery tube stops, but pushrod 216 keeps advancing distally to push matrix pellet 14 through the tube, out of the exit port 172 and into the interior 6 of the implanted device 2. Conical surface 238 captures the distal end 234 of the delivery tube and ensures alignment with the exit port 172.

Retraction spring 240 surrounds pushrod 216 and is restrained between proximal end 244 of delivery tube 210 and slide 220. The spring, therefore, causes delivery tube to advance distally with movement of slide and pushrod and compresses when delivery tube bottoms out and pushrod is advanced further. Advancement of the pushrod relative to the delivery tube serves to eject the matrix from the tube. After the matrix pellet 14 is pushed out of delivery tube, as shown in FIG. 5C, the slide may be released to permit pushrod to return to its retraced position. Delivery tube may be returned to its proximal position by proximal movement of the slide.

Prior to delivery of an implant and matrix, the obturator 180 is advanced distally to a delivery position, as shown in FIG. 5A, by screwing knob 183 so that knob threads 188 engage threaded sleeve 190. The delivery position of the obturator is reached after the threads of the knob have been advanced entirely through the threaded sleeve. In the delivery position, the support segment 184 of the obturator is advanced past the distal end 181 of the delivery device. In this configuration implant devices 2 or 40 may be manually loaded onto the support segment 184. Once mounted, the implant and underlying support segment 184 remain distal to the distal end 181 of the delivery device until the implant is placed in tissue and released In use, the intended tissue location is first accessed surgically, such as by a cut-down method. In the delivery position of the delivery device, the implant may be delivered into tissue by manually advancing the delivery device to the tissue location. With application of a delivery force, the sharp tip 176 of the obturator pierces the tissue permitting the obturator and implant to be pushed inward into the tissue until the distal end 181 of the device contacts the tissue indicating that the support segment 184 and implant have been fully inserted into the tissue. The advancement of the obturator and implant into the tissue may be aided by rotating the screw knob while applying the delivery force. The rotation may serve to provide a screwing action between the mounted implant and tissue being penetrated that will facilitate insertion. Retractable projecting barbs or vacuum suction may be added to the distal end of the delivery device to help maintain position of the distal end of the device on the tissue 26 during the matrix pellet delivery step that follows.

After the implant is placed in the tissue the obturator is disengaged by unscrewing the knob 183. Retraction spring 192 positioned around obturator shaft 182 so as to be biased between the inside surface 194 of knob 183 and proximal end 196 of body 200 is compressed while the obturator is advanced to the delivery position and thus serves to bias the obturator proximally so that threads 188 remain at the edge of engagement with threaded sleeve 190. Rotation of the knob 194 in the is counter-clockwise direction causes the threads 188 to immediately engage the threaded sleeve, permitting the assembly to be unscrewed, which causes obturator to be rotated and moved proximally. Rotation and proximal withdrawal of the obturator also causes the implant to be released from frictional engagement with the support region 184 of the obturator. The implant remains in the tissue as the obturator is with drawn. Release of the threads 188 from threaded sleeve 190 permits spring to expand to quickly force the obturator shaft fully proximally to complete disengagement from the inplant. The delivery tube then may be advanced to deliver the matrix. After the obturator is withdrawn, distal pressure is maintained on the body of the delivery device to ensure that the tapered portion 193 of the distal end 181 remains in the proximal end 12 of the implant to provide a pathway for the matrix delivery.

The delivery tube, preloaded with a matrix pellet may then be advanced distally by movement of the slide 220 as described above. During discharge of the matrix 14, the distal end of the device 181 should remain in position on the epicardial tissue surface 26 over the implant 2 to ensure tapered portion 193 remains in engagement with the implant 2, which ensures alignment of the exit port 172 with the interior 6 of the device 2, 40. After the matrix pellet is advanced into the interior of the implant, the slide is moved proximally, aided by the retraction spring to withdraw the pushrod and delivery tube. The delivery device may then be with drawn from the site.

From the foregoing it should be appreciated that the invention provides an agent delivery system for delivering an agent carrying pellet and implant device in combination. The invention is particularly advantageous in promoting angiogenesis within an ischemic tissue such as myocardial tissue of the heart. The delivery system is simple to use and requires a minimum of steps to practice.

It should be understood, however, that the foregoing description of the invention is intended merely to be illustrative thereof and that other modifications, embodiments and equivalents may be apparent to those skilled in the art without departing from its spirit.

What is claimed is:

1. A tissue implant and agent carrying matrix delivery system comprising:

a hollow tubular body defining an interior, distal end and distal port;

an obturator shaft having a proximal end, distal end, an implant device support section adjacent its distal end, a sharp distal tip and a handle at its proximal end for grasping and being advanceable through the interior of the body;

a matrix delivery tube, also advanceable through the interior of the body, having an interior lumen adapted to slidably receive an agent matrix, a push rod slidable through the lumen to advance the matrix through the tube and a distal end opened to the lumen;

a slide slidably mounted on the body and connected with the matrix delivery tube to advance the tube through the interior of the body with movement of the slide;

the obturator and matrix delivery tube being arranged so that each may be alternately advanced through the interior of the body to be placed in communication with the distal port.

2. A delivery device as defined in claim 1 further comprising:

a conical taper on the interior of the body near its distal end to help guide the obturator and matrix delivery tube to the distal port.

3. A delivery device as defined in claim 1 further comprising:

biasing members to bias the obturator and matrix delivery tube in retracted positions such that they do not extend through the distal port of the body.

4. A delivery device as defined in claim 1 wherein the device support section of the obturator is adapted to releaseably retain a tissue implant.

5. A delivery device as defined in claim 1 wherein the tubular body is rigid.

* * * * *